United States Patent [19]

Ishimura et al.

[11] Patent Number: 5,110,951
[45] Date of Patent: May 5, 1992

[54] METHOD FOR PRODUCING L-ASCORBIC ACID 2-PHOSPHATES

[75] Inventors: Yoshimasa Ishimura; Yohei Kurata, both of Kawasaki, Japan

[73] Assignee: Showa Denko K.K., Tokyo, Japan

[21] Appl. No.: 542,550

[22] Filed: Jun. 25, 1990

[51] Int. Cl.$^5$ .............................................. C07F 9/06
[52] U.S. Cl. .................................................. 549/222
[58] Field of Search ........................................ 549/222

[56] References Cited

U.S. PATENT DOCUMENTS 3,658,848  4/1972  Nomura et al. ................... 260/343.7
3,671,549  6/1972  Hinkley ............................. 260/343.7
4,179,445 12/1979  Sieb et al. ......................... 260/340.9

FOREIGN PATENT DOCUMENTS 0339486 11/1989  European Pat. Off. .
1805958  5/1969  Fed. Rep. of Germany .
2719303 11/1977  Fed. Rep. of Germany .
2063597  3/1987  Japan .

OTHER PUBLICATIONS

Chem. Pharm. Bull., 19(7) 1433-1437, (1971).

Primary Examiner—C. Warren Ivy
Assistant Examiner—Amelia A. Owens
Attorney, Agent, or Firm—Sughrue, Mion, Zinn, Macpeak & Seas

[57] ABSTRACT

A method for producing L-ascorbic acid 2-phosphates, is disclosed which comprises phosphorylating L-ascorbic acid whose hydroxyl groups at the 5- and 6-positions are unprotected or protected with a protective group, or salts thereof, with a phosphorus oxyhalide to form corresponding L-ascorbic acid 2-phosphates, wherein a reaction mixture obtained after the phosphorylation reaction is heated to convert by-products derived from L-ascorbic acid into L-ascorbic acid, which again is subjected to the phosphorylation reaction with the phosphorus oxyhalide. The method produce L-ascorbic acid 2-phosphates in a high yield and at a high purity with simple operations.

7 Claims, No Drawings

METHOD FOR PRODUCING L-ASCORBIC ACID 2-PHOSPHATES

BACKGROUND OF THE INVENTION

1. Field of the Invention

The present invention relates to a method for producing L-ascorbic acid 2-phosphates.

2. Description of Related Arts

L-Ascorbic acid (Vitamin C) is used widely in various fields such as drugs, foodstuffs, cosmetics and feedstuffs. L-Ascorbic acid is a reductive substance and has disadvantages that it has a poor stability because it is susceptible to heat and light and readily undergoes oxidation with oxygen in the air particularly when it is in a free state.

The instability is known to be due to ene-diol groups at the 2- and 3-positions of L-ascorbic acid structure. Therefore, the reductivity of L-ascorbic acid can be prevented by introducing appropriate substituents at one or both hydroxyl groups thereof, and hence the above-described defects of the acid can be removed.

Accordingly, various ascorbic acid derivatives have heretofore been proposed. It has been confirmed that among the conventional L-ascorbic acid derivatives, those derivatives which are derived by esterifying the hydroxyl group at the 2-position of L-ascorbic acid with phosphoric acid, i.e., L-ascorbic acid 2- phosphates, are readily hydrolyzed in vivo and exhibit vitamin C activity and are stable as well (cf. E. Cutolo and A. Larizza, Gazz. Chim. Ital. 91, 964 (1961)).

As for the method for the production of L-ascorbic acid 2-phosphates, there have heretofore been known those methods in which L-ascorbic acid or its salts or L-ascrobic acid derivatives of which the hydroxyl groups at the 5- and 6-positions have each been protected with a protective group are reacted with, for instance, phosphoric halide (cf. E. Cutolo and A. Larizza, Gazz. Chim. Ital. 91, 964 (1961), Chem. Pharm. Bull. 19(7) 1433 (1971), U.S. Pat. No. 3,671,549, and German Patent 1,805,958).

However, the above-described methods are disadvantageous as an industrial method because according to them, the hydroxyl groups at the 3-, 5- or 6-position are phosphorylated at the same time, thus producing several kinds of homologues and 2-pyrophosphates as by-produots in addition to the objective compounds to lower the yields of the objective compounds, and it is very difficult to separate the by-products, with the result that there are required very complicated purification steps and also a large amount of chemicals and many days for the separation, thus leading to increase in the production cost.

U.S. Pat. No. 3,858,848 discloses an improved method for the production of L-ascorbic acid 2-phosphate with its selectivity. Although the patent referred to a method for the synthesis of L-ascorbic acid 3-phosphate and it was considered at that time that the 3-position of L-ascorbic acid was esterified with phosphoric acid, it has recently been confirmed that what is actually esterified with phosphoric acid is the 2-position of L-ascorbic acid.

The above-described method is to react 5,6-isopropylidene-L-ascorbic acid or L-ascorbic acid with a phosphoric halide in a specific solvent (such as water, or a mixed solvent composed of water and acetone, dimethylformamide or trimethylphosphoric acid) in the presence of a base at temperature not higher than room temperature. More particularly, L-ascorbic derivative of which the hydroxyl groups at the 5- and 6-positions have been protected with acetone under acidic conditions (i.e., 5,6-isopropylidene-L-ascorbic acid) or L-ascorbic acid is dissolved in a mixed solvent composed of water and pyridine or a mixture of water and calcium hydroxide, and phosphorus oxychloride is added dropwise to the resulting solution or mixture at a temperature not higher than 0° C., and the reaction is continued at the same temperature for 90 minutes (reaction ratios: 94.5% and 70.6%, respectively). Then, the reaction mixture is treated with Amberlite Resin IR-120 (H+-form) at room temperature to desalt the product, followed by neutralization with magnesium oxide, removal of the solvent by distillation, dropwise addition of ethanol to the residue to obtain white powder of magnesium salt of L-ascorbic acid 2-phosphate, which is recrylstallized from water-ethanol (yields: 75.1% and 55.3%, respectively).

U.S. Pat. No. 4,179,445 discloses another improved method in which 5,6-isopropylidene-L-ascorbic acid, a phosphorus oxyhalide of general formula $POX_3$ (wherein X is a halogen atom) and a specific solvent (a mixed solvent composed of water and a tertiary amine) are mixed with each other and the mixture is kept at pH 13 or higher to react. More particularly, 5,6-isopropylidene-L-ascorbic acid is dissolved in a mixed solvent composed of water and pyridine, and phosphorus oxychloride is added dropwise to the mixture at $-10°$ C. to $+10°$ C. In this case, an aqueous solution of 10M sodium hydroxide is added dropwise to the mixture with stirring in order to carry out the reaction in a higher pH range (e.g., about pH 13). After completion of the reaction, the reaction mixture is cooled to room temperature, treated with a strongly acidic cation exchange resin (H+-form) for desalting and purification, followed by neutralization with magnesium oxide and removal of the solvent by distillation and dropwise addition of ethanol to the residue to give white powder of magnesium salt of L-ascorbic acid 2-phosphate, which is collected by filtration (yield: 86%).

However, what is common among the above-described improved methods is that the phosphorylation reaction is carried out at a temperature of not higher than 10° C., mostly not higher than 5° C. and various operations for overall steps of production are conducted while keeping ambient temperature at low temperatures which are not higher than room temperature. For this reason, a relatively large amount of by-products, i.e., bis(L-ascorbic acid) 2,2'-phosphate, bis(L-ascorbic acid) 2,3'-phosphate, bis(L-ascorbic acid) 3,3'-phosphate, L-ascorbic acid 3-phosphate and the like, are produced. These by-products have been abandoned after they were separated from the objective compounds in purification steps even though they occupy a large amount, e.g., 20 to 30%, of the total products of the reaction concerned.

As the result, the yield of the objective L-ascorbic acid 2-phosphate remains at a low level and means for separating and purifying the objective substance are very complicated and unsatisfactory as an industrial production method.

SUMMARY OF THE INVENTION

Therefore, it is an object of the present invention to provide a new, industrially advantageous method for producing L-ascorbic acid 2-phosphates by reacting L-ascorbic acid or its salt, or an L-ascorbic acid derivative of which the hydroxyl groups at the 5- and 6-positions are protected with a protective group with a phosphorus oxyhalide to give corresponding L-ascorbic acid 2-phosphates.

Under the circumstances, intensive investigation has been made on various conditions for the synthesis of L-ascrobic acid 2-phosphates, and as the result, it has now been found that the addition of an operation of "heating" to the phosphorylation reaction step with a phosphorus oxyhalide which has been commonly carried out at low temperatures results in the loss of the aforementioned by-products and most parts of them are reconverted into L-ascorbic acid, a part of which is converted into L-ascorbic acid 2-phosphates, thus accomplishing the present invention.

Therefore, the present invention provides a method for producing L-ascorbic acid 2-phosphates, comprising phophorylating L-ascorbic acid whose hydroxyl groups at the 5- and 6-positions are unprotected or protected with a protective group, or salts thereof, with a phosphorus oxyhalide to form corresponding L-ascorbic acid 2-phosphates, wherein a reaction mixture obtained after the phosphorylation reaction is heated to convert by-products derived from L-ascorbic acid into L-ascorbic acid, which again is subjected to the phosphorylation reaction with the phosphorus oxyhalide.

The above and other objects, effects, features and advantages of the present invention will become more apparent from the following description of embodiments thereof.

DETAILED DESCRIPTION OF THE INVENTION

Starting compound which can be used in the method of the present invention includes in addition to L-ascorbic acid, L-ascorbic acid derivatives in which the 5- and 6-positions are protected with a protective group, and their salts (hereafter, referred to collectively as "ascorbic acid compounds").

Specific examples of the L-ascorbic acid derivatives whose hydroxyl groups at the 5- and 6-positions are protected include 5,6-isopropylidene-L-ascorbic acid compounds, 5,6-benzylidene-L-ascorbic acid compounds, 5,6-cyclochexylidene-L-ascorbic acid compounds, and 5,6-sec-butylidene-L-ascorbic acid compounds. Amoung them, preferred are 5,6-isopropylidene-L-ascorbic acid compounds.

Suitable examples of the salts of L-ascorbic acid and of its derivatives include sodium salts, potassium salts, calcium salts, and magnesium salts.

Specific examples of the phosphorus oxyhalides include phosphorus oxychloride, phosphorus oxybromide, phosphorus oxyfluoride and phosphorus oxyiodide. Among them, preferred is phosphorus oxychloride.

The phosphorus oxyhalide is used in various amounts depending on the kind of solvents used, reaction temperature and also on the kind of phosphorus oxyhalide itself. Usually, it is used in about an equimolar or double molar amount based on the L-ascorbic acid compound used as the starting compound or unreacted L-ascorbic acid compound which remains after the heating step.

Any solvents that have been used conventionally in the phosphorylation reaction of L-ascorbic acid compounds such as those described in U.S. Pat. Nos. 3,658,848 and 4,179,445. Specific examples of the solvent include solvent systems such as water, and a mixed solvent composed of water and acetone, dimethylformamide or trimethylphosphoric acid, which contain an inorganic base such as sodium hydroxide, potassium hydroxide, calcium hydroxide, sodium carbonate, potassium carbonate, calcium carbonate, or calcium oxide, or an organic base such as ammonia, dimethylamine, trimethylamine or pyridine (cf. U.S. Pat. No. 3,658,848), and those solvent systems which comprises a mixed solvent composed of water and pyridine and an additives such as an alkali metal hydroxide (e.g., sodium hydroxide, potassium hydroxide and the like), and an alkali metal carbonate (e.g., sodium carbonate, potassium carbonate, calcium carbonate and the like), to which the above-described alkali metal salts are added in order to maintain their pH value in an alkaline range (cf. U.S. Pat. No. 4,179,445).

In the method of the present invention, the reaction between the L-ascorbic acid compounds and the phosphorus oxyhalide can be carried out at a temperature not higher than room temperature. However, it is not always necessary to restrict the reaction temperature at low temperatures and the phosphorylation reaction can be carried out at room temperature or at about 40° C. This is due to the feature of the present invention that by-products which increase during the phosphorylation reaction are hydrolyzed under heating to be converted back into L-ascorbic acid by elevating the reaction temperature in the subsequent heating step.

As stated above, it is also an important feature of the method of the present invention that the control of the reaction temperature is facilitated as compared with the conventional production methods.

After the phosphorylation reaction, the reaction mixture containing the L-ascorbic acid 2-phosphates is heated at 50° to 150° C. for 1 to 200 minutes, preferably at 80° to 110° C. for 5 to 100 minutes, to thermally decompose the by-products in the reaction mixture so that they can be converted back into L-ascorbic acid.

In this case, it has also been found that a part of the by-products (bis(L-ascorbic acid) 2,3'-phosphates) is converted into the objective L-ascorbic acid 2-phosphate upon the thermal decomposition.

L-ascorbic acid which is formed upon the thermal decomposition of the by-products is converted into L-ascorbic acid 2-phosphate by carrying out again the phosphorylation reaction.

The thermal decomposition and the phosphorylation reaction can be performed batch-wise or continuously. That is, a reactor for the phosphorylation reaction and a thermal reactor for the thermal decomposition of the by-products can be connected to each other in series, and L-ascorbic acid or its salt or a derivative of L-ascorbic acid or its salt of which the 5- and 6-positions are substituted with a protective group is phosphorylated with a phosphorus oxyhalide and the reaction mixture is supplied to the thermal reactor, in which by-products produced during the phosphorylation reaction are converted into L-ascorbic acid, which is then backed to the phosphorylation reactor and phosphorylated, thus achieving a continuous reaction.

As stated above, according to the method of the present invention, the yield of the objective compound, L-ascorbic acid 2-phosphate, can be increased and minimizing or avoiding the occurrence of the by-products by repeating the "phosphorylation reaction" and "thermal decomposition".

When the heating temperature is not higher than 90° C., time required for decomposition becomes longer according as the heating temperature is decreased. For example, the decomposition requires 20 minutes at 80° C. and on the other hand 40 minutes at 70° C., which shows a tendency that the decomposition proceeds almost kinetically.

After completion of the reaction, the reaction mixture is purified by a conventional method such as column chromatography. When the derivatives of L-ascorbic acid or its salt of which the 5- and 6-positions are substituted with a protective group are used as a starting compound, the protective group is readily hydrolyzed in the presence of water and the derivatives are converted into L-ascorbic acid or its salts.

The objective compound can be purified further as sodium, potassium, magnesium or calcium salt by recrystallization.

According to the method of the present invention, L-ascorbic acid 2-phosphates can be produced in higher yields with a simpler manner than the conventional methods. The compounds obtained are colorless, highly pure products which do not give rise to impurities in an aqueous solution.

EXAMPLES

Hereafter, the present invention will be described in greater detail with reference to examples. However, it should not be construed that the present invention is limited to the examples. In the examples, all percentages and parts are by weight unless otherwise indicated.

EXAMPLES 1

L-Ascorbic acid (6.76 g), 80 ml of deionized water and 6.08 g of pyridine were mixed and dissolved. An aqueous solution of 15.91 g of potassium carbonate in 20 ml of deionized water and 7.66 g of phosphorus oxychloride were dropwise added by turns to the resulting solution in 15 minutes while stirring at 20° C. or lower. After completion of the reaction, the reaction mixture, which contained 52% of L-ascorbic acid 2-phosphate and 31% of by-products, as it is, was heated at 90° C. for 10 minutes. Then, the content of L-ascorbic acid 2-phosphate reached 54% and that of the by-products decreased to 7%. Most of the by-products were converted by decomposition back into L-ascorbic acid and a part of which was converted into the objective compound. The reaction mixture was cooled to room temperature, and an aqueous solution of 6.12 g of potassium carbonate in 7.7 ml of deionized water and 2.95 g of phosphorus oxychloride were dropwise added thereto by turns in 15 minutes while stirring. After completion of the reaction, the reaction mixture contained 69% of L-ascorbic acid 2-phosphate and 20% of by-products. After heating the reacion mixture at 90° C. for 10 minutes in the same manner as described above, the content of L-ascorbic acid 2-phosphate became 70% and that of the by-products became 6%. After cooling it, the reaction mixture was treated with Amberlite IRA-68 (Cl−-form) resin and as the result unreacted L-ascorbic acid, pyridine and the by-products were removed readily. The thus-purified solution was neutralized with magnesium oxide and the aqueous solution was neutralized with magnesium oxide and the aqueous solution thus prepared was concentrated to a concentration of 1/10 time the original. Then, a double amount of methanol was added to give white crystals, which were collected by filtration to obtain magnesium salt of L-ascorbic acid 2-phosphate. Recrystallization of the compound from water/methanol afforded 7.02 g of the objective compounds as white crystals (yield: 50.6%).

EXAMPLE 2

L-ascorbic acid (6.76 g), 80 ml of deionized water and 6.08 g of pyridine were mixed and dissolved. An aqueous 48% solution of sodium hydroxide (16.2 g) and 6.48 g of phosphorus oxychloride were dropwise added by turns to the resulting solution in 15 minutes while stirring at 40° C. After completion of the reaction, the reaction mixture contained 47% of L-ascorbic acid 2-phosphate and 30% of by-products. The resulting mixture was heated at 90° C. for 10 minutes. Then, the content of L-ascorbic acid 2-phosphate reached 50% and that of the by-products decreased to 7%. To this were dropwise added by turns an aqueous 48% solution of sodium hydroxide (8.9 g) and 2.95 g of phosphorus oxychloride in 6 minutes while stirring at 40° C. After completion of the reaction, the reaction mixture contained 64% of L-ascorbic acid 2-phosphate and 19% of by-products. The resulting mixture was heated at 90° C. for 10 minutes in the same manner as described above. Then, the content of L-ascorbic acid 2-phosphate reached 65% and that of the by-products decreased to 6%. By treating the reaction mixture in the same manner as in Example 1, 5.97 g of the objective compound was obtained as white crystals (yield: 43.0%).

EXAMPLE 3

L-ascorbic acid (30.92 g), 365 ml of deionized water and 27.81 g of pyridine were mixed and dissolved. The resulting mixture was allowed to react continuously using an apparatus of the construction as described below. That is, an apparatus was used which was constructed by a circuit which comprised a 200 ml three-necked flask (reactor A) and a 500 ml three-necked flask (reactor B) and a polyvinyl chloride tube which connected flasks A and B serially as well as a circulation pump (IWAKI METERING PUMP EX-C60 type, produced by IWAKI CO., LTD.) which was adapted to circulate the reaction mixture in the circuit at a flow rate of 20 ml per minute. The mixture was charged in the apparatus and while it was being circulated therein the reactor A was cooled on an ice bath to maintain the temperature of the liquid in the reactor A at 15° to 20° C. On the other hand, the reactor B was heated on a silicone oil bath to maintain the temperature of the liquid in the reactor B at 55° to 70° C. Thereafter, phosphorus oxychloride and the aqueous solution of sodium hydroxide were dropwise added in 5 hours at 15 to 20° C. under the following conditions. That is, phosphorus oxychloride was dropwise added at a rate of 9.63 ml per hour using a microfeeder (MODEL MF-2 type, produced by HIGASHI DENKI KOGYO CO., LTD.) and at the same time an aqueous solution of sodium hydroxide (56.32 g of sodium hydroxide in 126 ml of deionized water) was dropwise added at a rate of 28 ml per hour using a pump (MICROTUBE PUMP MP-3 type, produced by TOKYO RIKA KIKAI CO., LTD.). While maintaining the temperature of the liquid within the reactor B at 55° to 70° C., the above-described reaction mixture was circulated therein at a rate of 20 ml/minute, and the reaction was completed after 5 hours. The resulting reaction mixture was treated in the same manner as in Example 1 to obtain 26.7 g of the objective compound as white crystals (yield: 42%).

The invention has been described in detail with respect to embodiments, and it will now be apparent from the foregoing to those skilled in the art that changes and modifications may be made without departing from the invention in its broader aspects, and it is the invention, therefore, in the appended claims to cover all such changes and modifications as fall within the true spirit of the invention.

What is claimed is:

1. A method for producing L-ascorbic acid 2-phosphate comprising:
   (a) phosphorylating L-ascorbic acid having hydroxyl groups at the 5- and 6-positions which are unprotected or protected with a protective group, or a salt thereof using a phosphorus oxyhalide at a temperature not higher than about 40° C. to form a reaction mixture containing L-ascorbic acid 2-phosphates,
   (b) heating the reaction mixture resulting from step (a) to convert by-products derived from phosphorylating L-ascorbic acid in step (a) at a temperature of about 50° to about 105° C. into L-ascorbic acid, and
   (c) phosphorylating the reaction mixture containing said L-ascorbic acid from step (b) using a phosphorus oxyhalide at a temperature not higher than about 40° C.

2. A method for producing L-ascorbic acid 2-phosphate, comprising:
   (a) phosphorylating L-ascorbic acid having hydroxyl groups at the 5- and 6-positions which are unprotected or protected with a protective group, or a salt thereof using a phosphorus oxyhalide at a temperature not higher than about 40° C. to form a reaction mixture containing L-ascorbic acid 2-phosphates,
   (b) heating the part of the reaction mixture resulting from step (a) containing by-products derived from phosphorylating L-ascorbic acid at a temperature of about 50° to about 105° C. to convert said by-products into L-ascorbic acid, and
   (c) phosphorylating the reaction mixture containing said L-ascorbic acid from step (b) using a phosphorus oxyhalide at a temperature not higher than about 40° C.;
   wherein a part of the reaction mixture is converted into L-ascorbic acid 2-phosphates.

3. A method as claimed in claims 1 or 2, wherein said method comprises repeating said heating step (b) and said phosphorylation step (c) at least 2 times.

4. A method for producing L-ascorbic acid 2-phosphate, comprising:
   (a) phosphorylating L-ascorbic acid or its salt or a derivative of L-ascorbic acid or its salt having the 5- and 6-positions substituted with a protective group using a phosphorus oxyhalide at a temperature not higher than about 40° C. in a phosphorylation reactor;
   (b) supplying the reaction mixture from step (a) to a thermal decomposition reactor;
   (c) heating the reaction mixture in said thermal decomposition reactor at a temperature of about 50° to about 150° C. to convert by-products formed during the phosphorylation reaction of step (a) into L-ascorbic acid, and
   (d) feeding L-ascorbic acid obtained from step (c) back to said phosphorylation reactor to phosphorylate the L-ascorbic acid;
   wherein said phosphorylation reactor and said thermal decomposition reactor are connected serially to each other.

5. The method of claim 1, wherein step (a) and step (c) are each conducted at a temperature of about room temperature to a temperature not higher than about 40° C.

6. The method of claim 2, wherein step (a) and step (c) are each conducted at a temperature of about room temperature to a temperature not higher than about 40° C.

7. The method of claim 4, wherein step (a) is conducted at a temperature of about room temperature to a temperature not higher than about 40° C.

* * * * *